(12) United States Patent
Peterson et al.

(10) Patent No.: US 9,155,867 B2
(45) Date of Patent: Oct. 13, 2015

(54) CATHETER SECUREMENT VIA INTEGRATED SECUREMENT STRIPS

(75) Inventors: Bart D. Peterson, Farmington, UT (US); Zachary Graham Forbes, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/117,828

(22) PCT Filed: May 21, 2012

(86) PCT No.: PCT/US2012/038865
§ 371 (c)(1),
(2), (4) Date: Jan. 21, 2014

(87) PCT Pub. No.: WO2012/162251
PCT Pub. Date: Nov. 29, 2012

(65) Prior Publication Data
US 2014/0128814 A1    May 8, 2014

Related U.S. Application Data

(60) Provisional application No. 61/488,322, filed on May 20, 2011.

(51) Int. Cl.
*A61M 25/02* (2006.01)

(52) U.S. Cl.
CPC ......... *A61M 25/02* (2013.01); *A61M 2025/026* (2013.01); *A61M 2025/028* (2013.01); *A61M 2025/0253* (2013.01)

(58) Field of Classification Search
CPC ............... A61M 2025/0253; A61M 2025/024; A61M 2025/026
See application file for complete search history.

(56) References Cited

U.S. PATENT DOCUMENTS

| | | | |
|---|---|---|---|
| 4,114,626 A | 9/1978 | Beran | |
| 4,224,937 A | 9/1980 | Gordon | |
| 4,737,143 A * | 4/1988 | Russell | 604/180 |
| 5,187,888 A * | 2/1993 | O'Brien et al. | 40/359 |
| 5,215,532 A * | 6/1993 | Atkinson | 604/180 |
| 5,800,401 A * | 9/1998 | Decker | 604/174 |
| 6,165,156 A | 12/2000 | Cesarczyk et al. | |
| 7,027,877 B2 * | 4/2006 | Dupelle et al. | 607/142 |
| 2003/0040788 A1 | 2/2003 | Dupelle et al. | |
| 2003/0055382 A1 | 3/2003 | Schaeffer | |
| 2009/0000972 A1 * | 1/2009 | Bartusiak | 206/411 |

FOREIGN PATENT DOCUMENTS

| | | |
|---|---|---|
| WO | 98/47556 | 10/1998 |
| WO | 2010/039751 A1 | 4/2010 |

* cited by examiner

*Primary Examiner* — Kami A Bosworth
*Assistant Examiner* — James Ponton
(74) *Attorney, Agent, or Firm* — Jeanne Lukasavage; Craig Metcalf; Kirton McConkie

(57) ABSTRACT

An intravenous catheter device is provided which includes an integrated adhesive strip whereby to secure the catheter adapter to the skin of a patient following catheterization. Some aspects of the present invention further comprise an adhesive strap that is coupled to the catheter adapter of a catheter assembly. One end of the adhesive strap is removed from the catheter adapter and wrapped around a body part or surface of the patient, and secured back to the catheter adapter. Thus, the catheter assembly is secured to the patient via the adhesive strap.

8 Claims, 4 Drawing Sheets

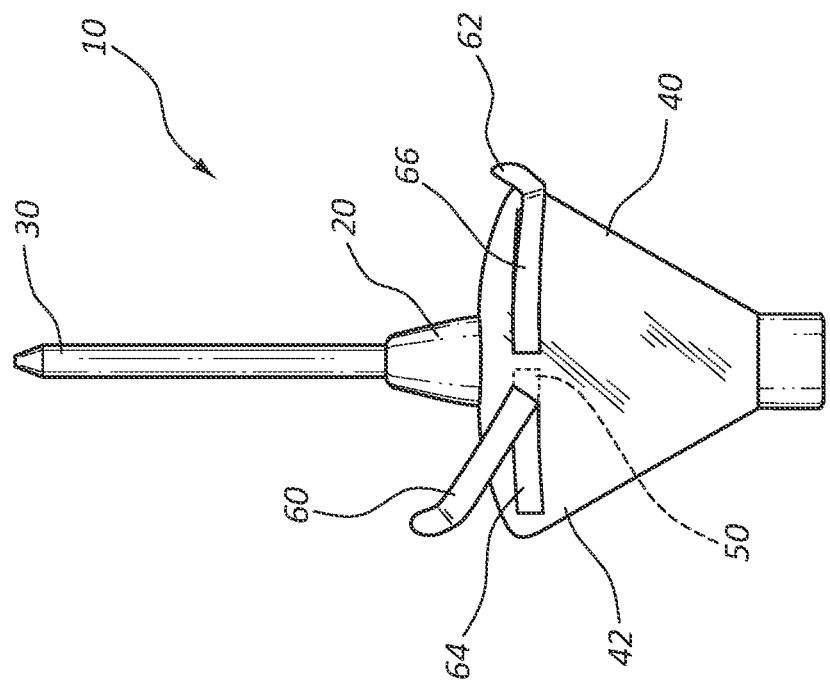
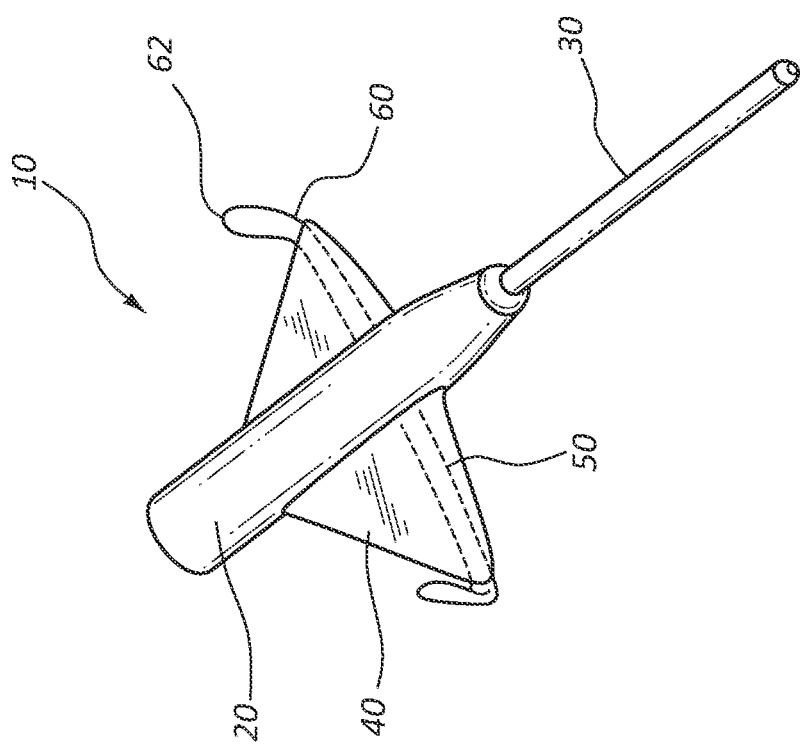

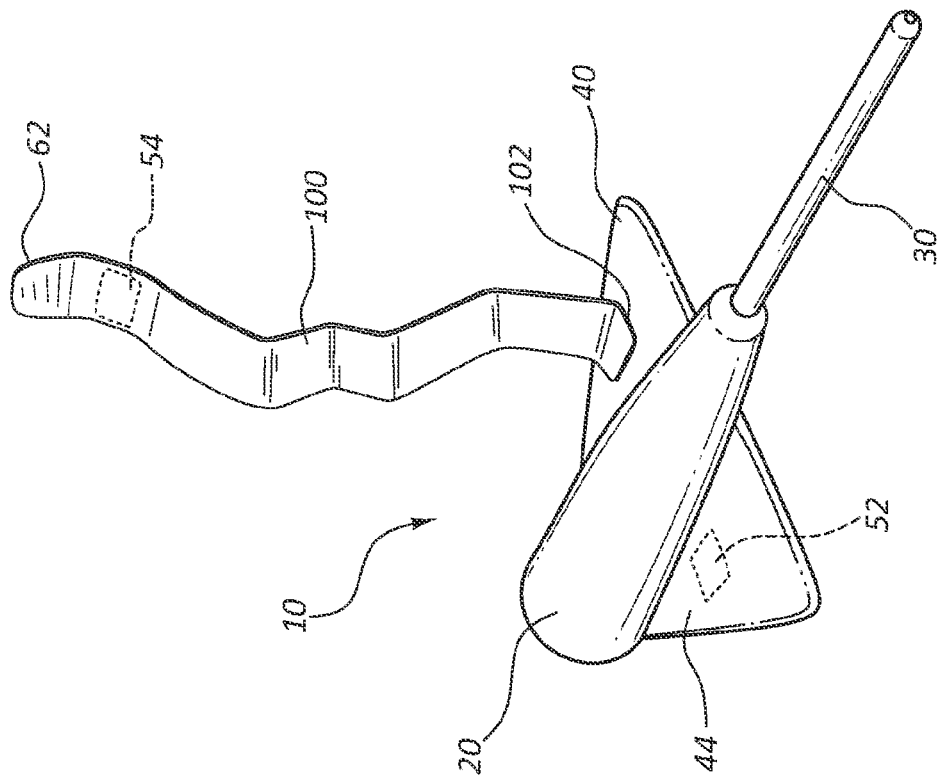
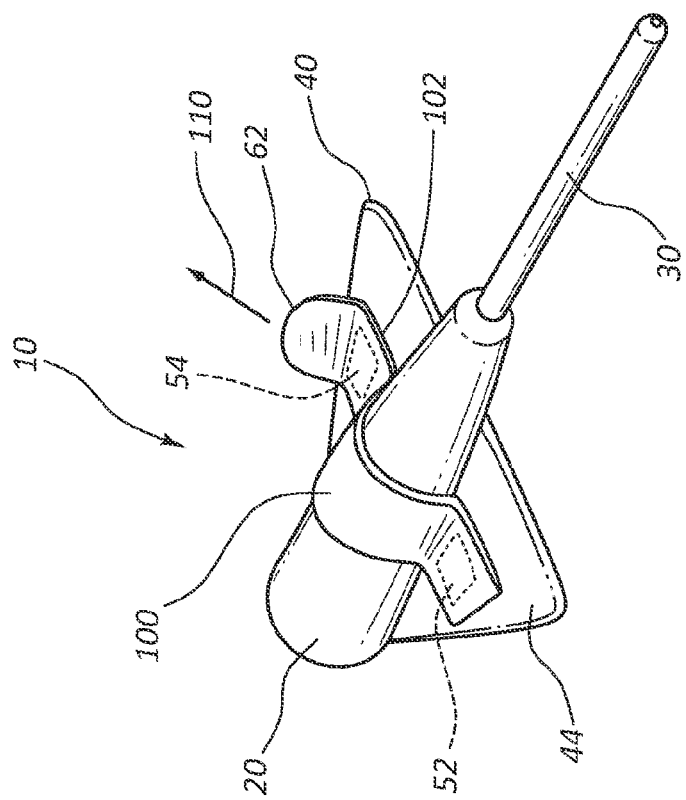
FIG. 2B
FIG. 2A

CATHETER SECUREMENT VIA INTEGRATED SECUREMENT STRIPS

This application is a National Stage of International Application No. PCT/US2012/038865, filed May 21, 2012, and entitled CATHETER SECUREMENT VIA INTEGRATED SECUREMENT STRIPS, which claims the benefit of U.S. Provisional Application No. 61/488,322, filed May 20, 2011. This application claims priority to and incorporates herein by reference the above-referenced application in its entirety.

BACKGROUND OF THE INVENTION

This disclosure relates generally to intravenous catheters. More specifically, this disclosure discusses various methods and systems for incorporating adhesive strips or other securement straps to an intravenous catheter to permit temporary securement of the intravenous catheter to a patient.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following catheterization, the intravenous catheter assembly is secured to the patient to prevent premature and/or unintended removal of the catheter assembly. In some instances, the clinician holds the inserted catheter assembly in place by digital pressure while preparing and applying adhesive strips to the catheter assembly. This process generally requires both hands of the clinician, and therefore the clinician commonly prepares the adhesive strips prior to inserting the catheter assembly into the patient. In other instances, a first clinician catheterizes the patient while a second clinician prepares and applies the adhesive strips to secure the inserted catheter assembly. Thus, the process of securing the inserted catheter assembly to the patient can be cumbersome and time consuming. Accordingly, there is a need in the art for a device which overcomes the difficulties and shortcomings associated with currently available technologies. The present disclosure discusses such a device.

BRIEF SUMMARY OF THE INVENTION

This disclosure relates generally to intravenous catheters. More specifically, this disclosure discusses various methods and systems for incorporating adhesive strips or other securement straps to an intravenous catheter to permit temporary securement of the intravenous catheter to a patient.

Some aspects of the present invention provide an intravenous catheter device having an integrated catheter securement adhesive strip or strap. An integrated catheter securement adhesive strip is provided on an underside of a catheter adapter, and more specifically on the underside of a securement platform or winged extensions which form a portion of the catheter adapter, or are coupled thereto. An adhesive strip is generally positioned so as to form a bond with the skin of a patient following catheterization. In some instances, an adhesive strip further includes a non-adhesive backing whereby to protect the adhesive properties of the adhesive strip prior to use. A non-adhesive backing is further desirable to prevent adhesion between the adhesive strip and the skin of the patient during catheterization, or for those instances where the clinician does not desire to adhere the catheter assembly to the patient.

In some implementations of the present invention, an adhesive strip is provided in a folded or multi-folded configuration to reduce the overall stored size of the strip prior to use. Adhesive material may be applied between adjacent or interfacing surfaces of the adhesive strip to maintain the folded configuration. Further, adhesive material may be applied between adjacent or interfacing surfaces of the adhesive strip to preserve the adhesive properties of the glue prior to use.

In some instances, an adhesive strap comprises a first end that is secured to a top or upper surface of a winged extension, such that a free end of the adhesive strap may be wrapped around a body part or surface of a patient and secured back to the winged extension at a position opposite the first end of the strap. For example, the free end of the adhesive strap may include an adhesive patch that is secured to the winged extension at a position opposite the first end of the strap. The adhesive strap may comprise a flexible or elastic material thereby allowing the strap to be stretched around a body part or other surface of the patient. Thus, the adhesive strap is utilized to secure the catheter assembly to a surface of a patient following catheterization.

In some implementations, a catheter assembly is provided having a catheter adapter which includes a proximal end, a distal end, and a middle section extending therebetween, wherein the middle section includes a securement platform or winged extension having an underside and an outer edge. The assembly further includes an adhesive strip applied to the underside of the securement platform. Some embodiments further include a non-adhesive backing applied to the adhesive strip, the non-adhesive backing having a pull tab positioned beyond the outer edge. The catheter assembly may further include a plurality of adhesive strips. In at least one embodiment, the adhesive strip comprises the entire underside of the catheter adapter and/or the securement platform.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which:

FIG. 1A illustrates a top perspective view of a catheter assembly having integrated adhesive strips in accordance with a representative embodiment of the present invention.

FIG. 1B illustrates a bottom view of the catheter assembly shown in FIG. 1, further illustrating a partially removed wax paper backing thereby exposing the adhesive of the catheter assembly in accordance with a representative embodiment of the present invention.

DETAILED DESCRIPTION OF THE INVENTION

Figure 2C:
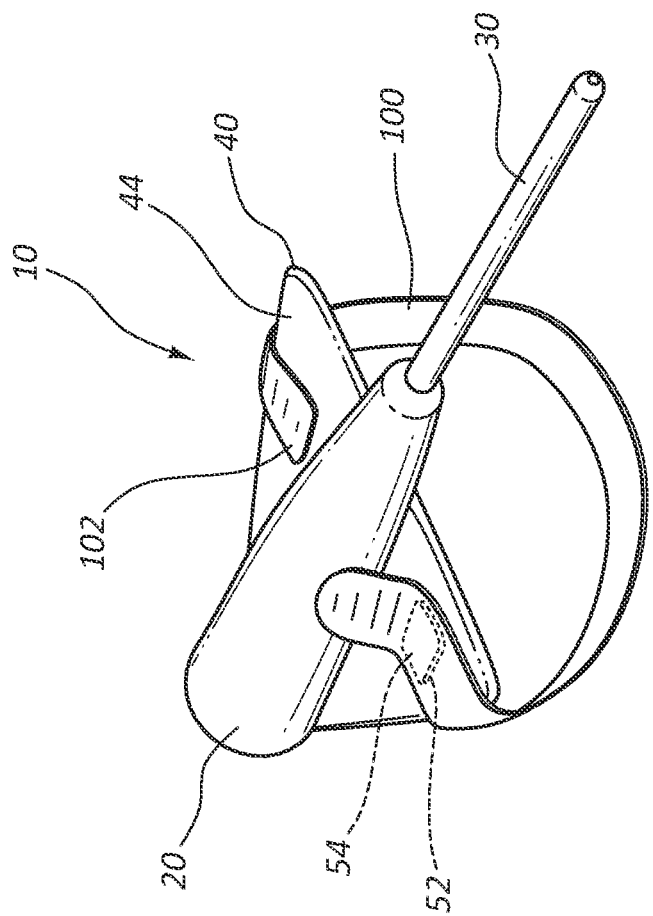
FIG. 2, shown in parts A-C, illustrates a catheter assembly having an integrated securement strap in accordance with a representative embodiment of the present invention.

The presently preferred embodiments of the described invention will be best understood by reference to the Figures, wherein like parts are designated by like numerals throughout. It will be readily understood that the components of the present invention, as generally described and illustrated in the accompanying Figures, could be arranged and designed in a wide variety of different configurations. Thus, the following more detailed description of some embodiments of the invention, as represented in the Figures, is not intended to limit the scope of the invention, as claimed, but is merely representative of some presently preferred embodiments of the invention.

Generally, the present invention relates to various systems and methods for securing a catheter assembly to a patient following catheterization. In some instances, the present invention provides one or more adhesive strips which are positioned and configured to temporarily maintain a position of a catheter assembly following catheterization. The adhesive strips are configured such that a clinician may insert the catheter assembly into the patient, adjust the catheter adapter of the catheter assembly to a desired position, remove protective, non-adhesive wax paper backings from the adhesive of the positioned catheter assembly, and temporarily fix the position of the catheter assembly at the desired position by contacting the exposed adhesive to the skin of the patient. In some instances, the exposed adhesive temporarily fixes the position of the catheter assembly, thereby allowing the clinician to gather and apply the final materials for longer-term securement of the catheter assembly to the patient. In other instances, the exposed adhesive provides long-term adhesion between the catheter assembly and the patient.

Referring now to FIGS. 1A and 1B, an intravenous catheter assembly 10 is shown. Intravenous catheter assembly 10 generally comprises a catheter adapter 20 having a distal end to which is secured an intravenous catheter 30. In some embodiments, catheter adapter 20 further comprises a securement platform or winged extensions 40 which interface with the skin of the patient to stabilize a desired position of catheter assembly 10 following catheterization. In some instances, winged extensions 40 are flexible or semi-flexible thereby allowing winged extensions 40 to contour and conform to the surface of the patient. Winged extensions 40 further prevent catheter assembly 10 from rolling about the central axis of catheter adapter 20 when placed on patient's skin.

In some embodiments, winged extensions 40 further comprise one or more adhesive strips 50 which are positioned on the underside 42 of extensions 40. Adhesive strips 50 are positioned so as to maintain a desired position of catheter adapter 20 following catheterization. In some embodiments, adhesive strips 50 further comprise wax paper strips or backings 60 which are placed over adhesive strips 50 to preserve the strips' adhesive properties prior to securement to the patient. Wax paper backings 60 further prevent premature securement of catheter assembly 10 to the patient, thereby allowing the clinician to freely move and position catheter assembly 10 prior to final securement. In some embodiments, adhesive strips 50 and wax paper backings 60 are positioned on catheter assembly 10 such that the clinician's technique is not hindered, or does not require adjustment when inserting catheter assembly 10 into the patient. Thus, a clinician may utilize the same technique for inserting catheter assembly 10 into a patient regardless of whether or not the clinician utilizes adhesive strips 50 to secure catheter assembly 10 to the patient.

Adhesive strips 50 may include any type or form of adhesive that is compatible with the teachings of the present invention. For example, in some embodiments adhesive strip 50 comprises a polymer-based pressure sensitive adhesive. As such, a bond is formed between adhesive strip 50 and the patient's skin by applying light pressure between winged extension 40 and the skin. Adhesive strip 50 may further comprise a slight liquid carrier that facilitates bonding with the skin. In some instances, adhesive strip 50 comprises a single-use glue, wherein the adhesive strip loses its adhesive properties once removed from the skin. In other instance, adhesive strip 50 comprises a multiple-use glue, wherein the adhesive strip may be applied repeatedly to the skin of the patient. For example, a multiple-use glue may be desired to permit subsequent adjustment of the catheter assembly's position following securement with adhesive strips 50. This may be desirable for situations where the tip of the catheter becomes occluded within the vein, thereby requiring the catheter 30 to be moved slightly to reestablish patency. This may also be a desirable feature where the placement of the catheter assembly 10 becomes uncomfortable to the patient.

Further, in some instances adhesive strip 50 comprises a self-adhering adhesive, wherein the adhesive co-adheres to itself, but does not adhere well to other surfaces. Adhesive strip 50 may further include elastic properties which permit the strip to stretch and adhere to itself or another surface. In some instances, adhesive strip 50 may comprises a mechanical fastener, such as Velcro®, a snap, a hook and button, or other type of mechanical attachment.

Adhesive strip 50 may comprise any shape, pattern, size and/or configuration necessary to provide a desired adhesion between catheter assembly 10 and the skin of the patient. For example, in some embodiments adhesive strip 50 comprises a plurality of parallel lines. In other embodiments, adhesive strip 50 comprises one or more circles. Further, in some embodiments adhesive strip 50 covers the entire underside 42 of winged extensions 40.

Wax paper backings 60 are generally provided as a protective layer that is applied over adhesive strip 50 to preserve the adhesive properties of strip 50 prior to use. Wax paper backings 60 may include any material or combination of materials that permit temporary bonding between backings 60 and adhesive strip 50, wherein upon removal of backings 60 from adhesive strip 50, the adhesive is left undisturbed. Non-limiting examples of compatible materials for backings 60 include paper, plastic, metal foil, plastic coated paper, wax coated paper, wax coated plastic, plastic coated foil, and wax coated foil.

In some embodiments, wax paper backings 60 further comprise one or more pull tabs 62 which are positioned to enable easy access and removal of backings 60 from adhesive strips 50 following catheterization. Pull tabs 62 are generally provided so as to be exposed to the clinician when underside 42 of winged extension 40 is placed against the skin of the patient. Thus, following catheterization, the clinician may position catheter assembly 10 and secure the final position of catheter assembly 10 by removing backings 60 via pull tabs 62.

In some instances, wax paper backings 60 comprises a first half 64 which directly contacts adhesive strip 50, and a second half 66 having a first end coupled to first half 64, and a second end coupled to pull tab 62. First half 64 comprises a length and width approximately equal to a length and width of adhesive strip 50. Second half 66 comprises a length sufficient to position pull tab 62 beyond an outer edge of winged extensions 40. Thus, pull tab 62 is positioned to enable the clinician to grip and remove tab 62 thereby exposing adhesive strip 50 to the patient's skin. In some instances, a mild or slightly tacky adhesive is applied between first and second halves 64 and 66 to maintain a folded configuration of backing 60 prior to removing wax paper backing 60 from adhesive strip 50. In other embodiments, first and second halves 64 and 66 comprise self-adhering adhesive, thereby maintaining a folded configuration of the two halves prior to removing wax paper backing 60 from adhesive strip 50.

In some embodiments, pull tab 62 is pulled in an outward direction, such that adhesive strip 50 is exposed starting at an inner end of strip 50 and progressively exposed towards an outer edge of winged extension 40. In some embodiments, catheter assembly 10 comprises a single adhesive strip, a single backing, and a single pull tab. In other embodiments, catheter assembly 10 comprises two or more adhesive strips, a single backing, and a single pull tab. Further, in some embodiments catheter assembly 10 comprises two or more adhesive strips, two or more backings, and two or more pull tabs.

Referring now to FIGS. 2A-2C, a catheter assembly 10 is shown having an integrated adhesive strap 100 attached to the catheter adapter portion 20 of the device. In some embodiments, catheter assembly 10 is further modified to include an adhesive strap 100 that is folded and secured to a top surface 44 of winged extensions 40. Adhesive strap 100 facilitates securement of catheter assembly 10 to a surface of a patient by wrapping and securing adhesive strap 100 around a body part of the patient. For example, adhesive strap 100 may be wrapped and secured around the hand or finger of a patient to maintain the position of catheter assembly 10 on the back of the patient's hand.

In some instances, adhesive strap 100 comprises a plurality of folds that crisscrosses over catheter adapter 20 between left and right sides of winged extension 40. A terminal end 102 of strap 100 is permanently anchored to the top surface 44 of one of the winged extensions 40, while the top surface 44 of the opposite winged extension 40 comprises an adhesive patch 52 that temporarily retains strap 100 in a folded configuration, prior to use. Strap 100 further comprises a second adhesive patch 54 that further retains strap 100 in a folded configuration, prior to use.

Adhesive strap 100 is separated from top surface 44 as pull tab 62 is pulled in an upward and outward direction 110, thereby detaching strap 100 from adhesive patch 52 and separating strap 100 from adhesive patch 54. In some embodiments, adhesive strap 100 comprises an elastic material that is capable of stretching to increase its overall length. In other embodiments, adhesive strap 100 comprises various lengths dependent upon the age, size, or portion of the patient for which catheter assembly 10 is designed. Further still, in some embodiments adhesive strap 100 comprises a single size that may be selectively adjusted by adhering strap 100 to adhesive patch 52 at any position along the length of strap 100.

Figure 3A:
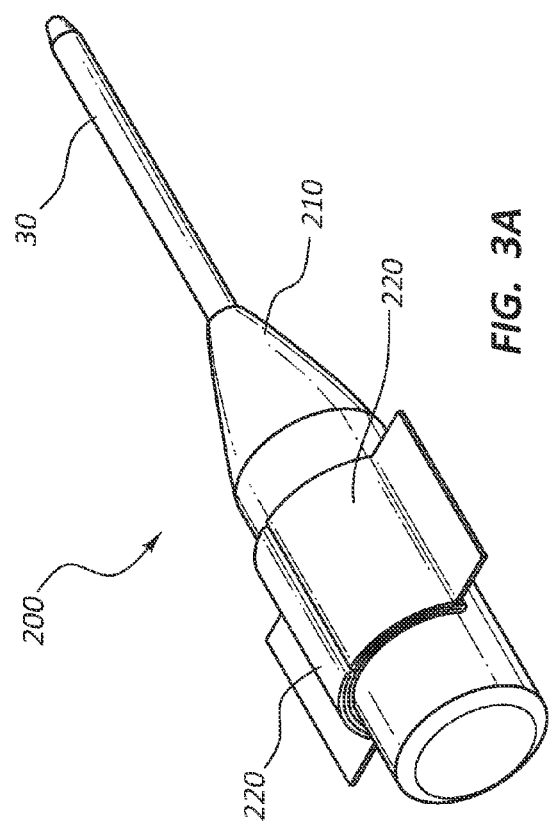
FIG. 3, shown in parts A-C, illustrates a catheter assembly having integrated securement strips in accordance with a representative embodiment of the present invention.
Figure 3B:
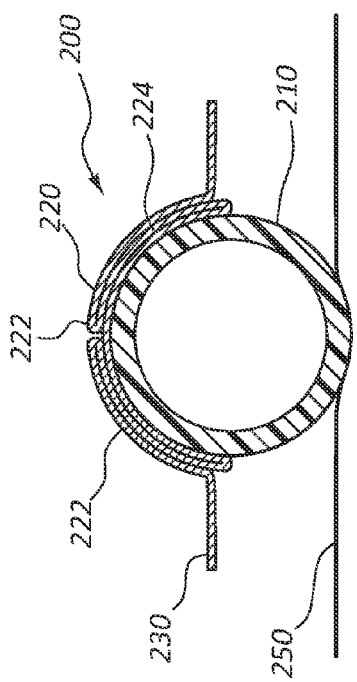
Figure 3C:
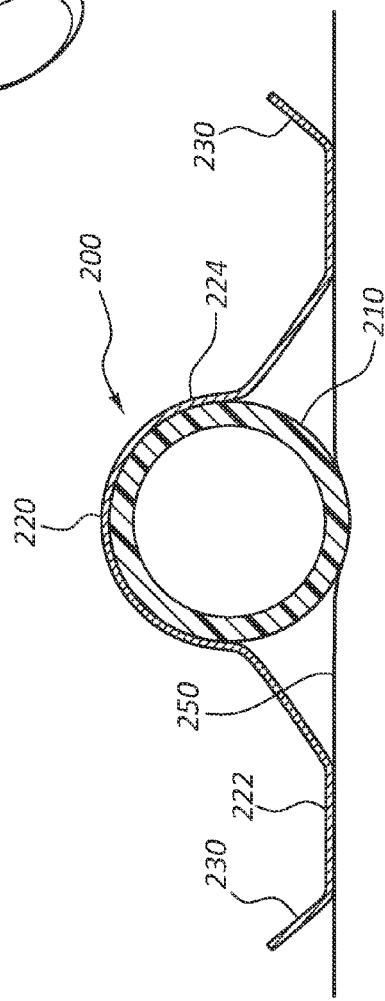

Referring now to FIG. 3, in some embodiments a non-winged catheter assembly 200 comprises an adhesive strip 220 having a middle portion or length permanently secured to the catheter adapter 210 via an adhesive. Prior to use, ends of adhesive strip 220 are folded closely against catheter adapter 210 such that the ends of adhesive strip 220 do not interfere with catheterization. In some instances, adhesive strip 220 comprises glue 222 interspersed between opposing inner surfaces of the ends of strip 220. Glue 222 serves to maintain the folded position of adhesive strip 220 prior to use. Adhesive strip 220 may further include additional glue materials on opposing portions of outer surface 224 which are in contact while in the folded configuration. These additional glue materials further assist in maintaining the folded position of adhesive strip 220 before use. Alternatively, outer surface 224 may comprise self-adhering adhesive.

Following catheterization, catheter adapter 210 is temporarily held in place by the clinician and secured to the patient 250 with adhesive strap 220. Adhesive strap 220 is removed from its folded position by pulling outwardly on pull tabs 230. Adhesive or glue 222 is exposed as adhesive strap 220 is unfolded. The portion of adhesive strap 220 comprising glue 222 is then applied to patient 250 thereby securing the position of catheter assembly 200.

The present invention may be embodied in other specific forms without departing from its structures, methods, or other essential characteristics as broadly described herein and claimed hereinafter. All of the described embodiments and examples are to be considered in any and all respects as illustrative only, and not restrictive. The scope of the invention is, therefore, indicated by the appended claims, rather than by the foregoing description. All changes that come within the meaning and range of equivalency of the claims are to be embraced within their scope.

The invention claimed is:

1. An intravenous catheter assembly, comprising:
   a catheter adapter;
   a catheter coupled to an end of the catheter adapter;
   a winged extension that extends from the catheter adapter, the winged extension comprising a first side, a second side, and a top surface; and
   a strap having a first portion and a second portion, a terminal end of the first portion being coupled to the top surface of the first side of the winged extension, the first portion extending from the first side to the second side of the winged extension overtop the catheter adapter, the second side including a first adhesive patch that secures the first portion to the second side, the second portion of the strap being folded backwards overtop the first portion, the second portion including a second adhesive patch that secures the second portion to the first portion, a terminal end of the second portion forming a pull tab for separating the second portion from the first portion and for separating the first portion from the second side of the winged extension thereby enabling the strap to be used to secure the intravenous catheter assembly to a portion of a patient's body by wrapping the strap around the portion of the patient's body and securing the second adhesive patch to the second side of the winged extension.

2. The assembly of claim 1, wherein the terminal end of the first portion is permanently coupled to the first side of the winged extension.

3. The assembly of claim 1, wherein the second adhesive patch adheres to the first adhesive patch when the strap is wrapped around the portion of the patient's body.

4. The assembly of claim 1, wherein the strap is elastic.

5. A catheter assembly, comprising:
a catheter adapter having an outer surface; and
an adhesive strip having a first side and a second side, the adhesive strip forming a middle portion, the first side of the middle portion being fixed to the outer surface of the catheter adapter, the adhesive strip further forming a first extension also having a first side and a second side and that extends from a first end of the middle portion, and a second extension also having a first side and a second side that extends from a second end of the middle portion, each of the first and second extensions including a first portion positioned adjacent the middle portion, a second portion positioned adjacent the first portion opposite the middle portion, and a pull tab positioned at an end of the extension opposite the middle portion;
wherein the first portion of each extension is folded backwards onto the middle portion, the second side of the first portion of each extension including an adhesive to secure the second side of the first portion of each extension to the second side of the middle portion;
wherein the second portion of each extension is folded backwards onto the first portion of the corresponding extension, the first side of the second portion of each extension including an adhesive for securing the first side of the second portion to the first side of the corresponding first portion and for securing the first side of the second portion to skin of a patient when the second portion is extended from the catheter adapter.

6. The assembly of claim 5, wherein the pull tab of each extension extends outwardly from the catheter adapter to facilitate extending the corresponding first and second portions of the extension from the catheter adapter.

7. The assembly of claim 5, wherein a combined length of the first portions is less than a length of the middle portion such that the first portions do not overlap when the first portions are folded back onto the middle portion.

8. The assembly of claim 5, wherein a length of the second portion of each extension is less than or equal to a length of the first portion of the corresponding extension such that the adhesive on the first side of the second portion is not exposed until the second portion is separated from the first portion.

* * * * *